United States Patent [19]

Heidlas et al.

[11] Patent Number: 5,616,352
[45] Date of Patent: Apr. 1, 1997

[54] PROCESS FOR THE PRODUCTION OF FAT- AND CHOLESTEROL-REDUCED POWERED PRODUCTS BASED ON EGGS WHICH ARE CHARACTERIZED BY A HIGH PHOSPHOLIPID CONTENT

[75] Inventors: Jürgen Heidlas, Trostberg; Heinz-Rüdiger Vollbrecht, Altenmarkt; Jan Cully, Garching, all of Germany

[73] Assignee: SKW Trostberg Aktiengesellschaft, Trostberg, Germany

[21] Appl. No.: 529,752

[22] Filed: Sep. 18, 1995

[30] Foreign Application Priority Data

Sep. 19, 1994 [DE] Germany ............... 44 33 274.2

[51] Int. Cl.$^6$ ........................ A23L 1/32
[52] U.S. Cl. ............... 426/312; 426/614; 426/425; 426/426; 554/206
[58] Field of Search ............... 426/614, 641, 426/694, 601, 603, 608, 417, 312, 425, 429; 554/206

[56] References Cited

U.S. PATENT DOCUMENTS

| | | | |
|---|---|---|---|
| 5,061,505 | 10/1991 | Cully et al. | 426/614 |
| 5,091,117 | 2/1992 | Athnasios et al. | 426/417 |
| 5,238,694 | 8/1993 | Ogasahara et al. | 426/614 |
| 5,288,619 | 2/1994 | Brown et al. | 426/601 |
| 5,466,842 | 11/1995 | Heidlas et al. | 426/614 |

FOREIGN PATENT DOCUMENTS

| | | |
|---|---|---|
| 0129739 | 1/1984 | European Pat. Off. . |
| 184023 | 5/1989 | European Pat. Off. . |
| 0352667 | 7/1989 | European Pat. Off. . |
| 0426425 | 10/1990 | European Pat. Off. . |
| 1123864 | 5/1989 | Japan . |
| 9302698 | 2/1993 | WIPO . |
| 9319617 | 10/1993 | WIPO . |

OTHER PUBLICATIONS

Heidlas, Jurgen E., "Propane Extraction in Food Processing," *Food Marketing & Technology*, Dec. 1994, pp. 38–43.

Eggers, R., et al., "High Pressure Extraction of Oil Seed," *Journal of the American Oil Chemists' Society*, vol. 62, No. 8, Aug. 1985, pp. 1222–1230.

Via, Jim C., et al., "Supercritical Fluid Fractionation of a Low Molecular Weight, High–Density Polyethylene Wax Using Carbon Dioxide, Propane, and Propane–Modified Carbon Dioxide," *Analytical Chemistry*, vol. 66, No. 5, Mar. 1, 1994, pp. 603–609.

*Primary Examiner*—Anthony J. Weier
*Attorney, Agent, or Firm*—Felfe & Lynch

[57] ABSTRACT

The present invention provides a process for the production of fat- and cholesterol-reduced powdered products based on eggs with a high content of phospholipids by extraction with compressed gases, wherein the powdered starting material is extracted with a solvent mixture consisting of propane and carbon dioxide with a mixing ratio of 95/5 to 5/95% by weight at a pressure of <300 bar and at s temperature of <70° C.,

8 Claims, No Drawings

PROCESS FOR THE PRODUCTION OF FAT- AND CHOLESTEROL-REDUCED POWERED PRODUCTS BASED ON EGGS WHICH ARE CHARACTERIZED BY A HIGH PHOSPHOLIPID CONTENT

The present invention is concerned with a process for the production of fat- and cholesterol-reduced powdered products based on eggs which are characterised by a high phospholipid content.

Cholesterol and cholesterol esters (in the following referred to as cholesterol derivatives) are fat-soluble compounds which occur in the fatty part of foodstuffs of animal origin, for example egg yolk and meat.

International health organisations recommend the populations of highly developed countries to restrict the intake of large amounts of fat and cholesterol since epidemological studies have clearly demonstrated a nutritionally-caused basis for arteriosclerosis and coronary heart disease.

Because of these recommendations, modern foodstuff technology has been encouraged to offer improved foodstuffs corresponding to the nutritional habits with a reduced content of fat and cholesterol. Decisive criteria are thereby that the organoleptic, nutritional-physiological and, from a foodstuff technological point of view, the functional properties of the products are substantially maintained.

With regard to the reduction of the cholesterol content, a series of processes is already known for the removal of cholesterol derivatives but, because of their low selectivity or because of the chemical change of important components of the starting material, for example denaturing of proteins, these processes are not suitable or not very suitable for reducing the cholesterol content of valuable foodstuffs.

In contradistinction thereto, high pressure extraction with supercritical carbon dioxide is a relatively gentle process for the removal of fats and cholesterol derivatives (cf. V. Krukonis, Supercritical Fluid Processes, International Symposium on Supercritical Fluids, Nice, 1988, and A. Bude and D. Knorr, Reduction of Cholesterol in Egg Powder and Whole Eggs by Extraction with Supercritical Carbon Dioxide, Fifth International Congress on Engineering and Food, 1989). However, all processes which work with supercritical carbon dioxide involve the disadvantages that very high process pressures (>250 bar) are necessary in order to achieve a corresponding gas loading and, furthermore, very high specific gas throughput rates are needed in order that the desired object of the extraction, namely a substantial reduction of the cholesterol content, is achieved. Consequently, the economic total balance of the carbon dioxide processes is, as a rule, so impaired that they can become uneconomic. Carbon dioxide extraction for the removal of cholesterol derivatives from egg yolk is described, for example, in EP-A-0 416 561.

In contradistinction to carbon dioxide, compressed propane in a relatively low pressure range shows a very good dissolving ability for fats and oils which has been used process-technically for quite a long time (cf., for example U.S. Pat. No. 2,560,935, U.S. Pat. No. 4,331,695 and DE-PS 23 63 418). A disadvantage of the propane extraction is the low selectivity with regard to the various lipophilic component materials, for example triglycerides, cholesterol derivatives and phospholipids.

It has already been suggested to improve the solubility of fats/oils or of fat-like materials in super-critical carbon dioxide by feeding into the extraction agent (carbon dioxide) divers entrainment agents, also including propane (cf. G. Brunner, Stofftrennung mit überkritischem Gasen, Chem.-Ing. Tech., 59, 12–22/1987). However, the technologically important aspects cannot be elucidated therefrom whether the selectivity of the extraction gases can be purposefully controlled in order to influence the extraction of certain components, especially phospholipids, and how the conditions necessary therefor can be ascertained.

Therefore, it is an object of the present invention to provide a process for the production of fat- and cholesterol-reduced powdered products based on eggs with compressed gases which does not display the mentioned disadvantages of the prior art but rather makes it economically possible drastically to reduce the amount of fats and cholesterol derivatives in the egg products without thereby removing comparatively large amounts of the technologically important phospholipids and especially of lecithin.

Thus, according to the present invention, there is provided a process for the production of fat- and cholesterol-reduced powdered products based on eggs with a high content of phospholipids by extraction with compressed gases, wherein the powdered starting material is extracted with a solvent mixture of propane and carbon dioxide in a mixing ratio of from 95/5 to 5/95% by weight at a pressure of <300 bar and a temperature of <70° C.

Surprisingly, we have found that, when maintaining these extraction conditions, the selective removal of the fats and cholesterol derivatives is sufficient, whereas the extraction of phospholipids can be purposefully controlled and thus can also be completely suppressed so that the functional properties of the egg product are fully maintained.

For the process according to the present invention, there are used powdered products based on eggs, for example egg yolk powder or whole egg powder or products which contain these materials. It is important for the present invention that the extraction with a mixture of propane and carbon dioxide is carried out in a mixing ratio of from 95/5 to 5/95% by weight at a pressure of <300 bar and a temperature of <70° C. In this way, it is ensured that the removal of the phospholipids is suppressed but the desired extraction of the fats and cholesterol derivatives takes place optimally.

Because of the sensitivity of the further component materials of egg products, especially of the protein part, the extraction is preferably carried out at an extraction temperature of from 20° to 60° C. and especially of from 30° to 50° C. Because of the low extraction pressures used and of the favourable specific gas throughput rates, the process according to the present invention is especially economic with propane/carbon dioxide mixtures of from 90/10 to 50/50% by weight and especially from 80/20 to 60/40% by weight. In this preferred working range, in which, according to the process of the present invention, the gas mixtures are present in liquid form, the extraction pressure can be from 10 to 100 bar. Due to the gentle process parameters, no denaturing of the proteins takes place. The amount of gas mixture used can be varied within wide limits and depends essentially on the amount of fats and cholesterol derivatives to be removed, as well as upon the composition of the extraction mixture: in the case of amounts of propane of >70% by weight, as a rule 1 to 30 kg per kg of starting material suffice in order to achieve a satisfactory reduction of the desired component materials. In the case of amounts of propane of <30% by weight, the necessary amount of gas can increase to 100 kg per kg of starting material in order to achieve the object of the extraction.

At the conclusion of the extraction, the extracted fats and cholesterol derivatives present dissolved in the compressed gas mixture can again be separated off from the solvent mixture by evaporation and/or pressure reduction. The gas mixture can then subsequently, after liquefaction and/or compression, be used again for the further extraction of egg products so that a small amount of gas mixture can be continuously circulated. In this way, the economy of the process can be distinctly increased.

Within the scope of the present invention, it is also possible, by variation of the extraction conditions, only partly to extract the fats from the egg products if, for any reason, this is desired. Thus, by variation of the extraction pressure, of the extraction temperature, as well as of the amount of gas, the ratio of fats to cholesterol derivatives can be purposefully controlled, the effectiveness of the process thereby being additionally increased.

With the help of the process of the present invention, it is possible to produce low cholesterol and low fat products based on eggs with good sensory properties, the cholesterol and fat content of which is reduced by more than 85%, the extraction of the phospholipids thereby being suppressed and these are highly enriched in the extraction residue.

The following Examples are given for the purpose of illustrating the present invention:

EXAMPLES.

The experiments were carried out in a high pressure extraction plant with an autoclave volume of 4 l. For the individual experiments, there was used an amount of 1000 to 1500 g of starting material.

The starting material investigated in Examples 1 to 6 (egg yolk powder) had the following composition in the lipid part:

| total fat | 64.3% by weight |
|---|---|
| cholesterol | 2.3% by weight |
| phospholipids | 17.5% by weight |

SM = solvent mixture
AM = starting material

EXAMPLE 1.

Comparative example with pure propane.

| Extraction medium: | propane |
|---|---|
| Process parameters: | |
| extraction pressure (bar) | 20 |
| extraction temperature (°C.) | 50 |
| SM/AM (kg/kg) | 15 |
| Extract: | |
| yield (% by wt.) | 43.6 |
| phospholipid content (% by wt.) | 5.25 |
| cholesterol content (% by wt.) | 4.9 |
| Residue (product): | |
| yield (% by wt.) | 55.1 |
| cholesterol content (% by wt.) | 0.14 |
| total fat (% by wt.) | 33.5 |
| phospholipids in the total fat (% by wt.) | 81 |
| phospholipids in the residue, abs. (% by wt.) | 27.1 |

EXAMPLE 2.

Comparative example with pure carbon dioxide.

| Extraction medium: | carbon dioxide |
|---|---|
| Process parameters: | |
| extraction pressure (bar) | 300 |
| extraction temperature (°C.) | 50 |
| SM/AM (kg/kg) | 130 |
| Extract: | |
| yield (% by wt.) | 38.5 |
| phospholipid content (% by wt.) | 0.1 |
| cholesterol content (% by wt.) | 5.9 |
| Residue (product): | |
| yield (% by wt.) | 58.4 |
| cholesterol content (% by wt.) | 0.15 |
| total fat (% by wt.) | 40 |
| phospholipids in the total fat (% by wt.) | 75 |
| phospholipids in the residue, abs. (% by wt.) | 30 |

EXAMPLE 3.

| Extraction medium: | propane/carbon dioxide |
|---|---|
| mixing ratio | 90/10 |
| Process parameters: | |
| extraction pressure (bar) | 30 |
| extraction temperature (°C.) | 50 |
| SM/AM (kg/kg) | 15 |
| Extract: | |
| yield (% by wt.) | 41.6 |
| phospholipid content (% by wt.) | 3.75 |
| cholesterol content (% by wt.) | 5.4 |
| Residue (product): | |
| yield (% by wt.) | 56.3 |
| cholesterol content (% by wt.) | 0.14 |
| total fat (% by wt.) | 36.3 |
| phospholipids in the total fat (% by wt.) | 76 |
| phospholipids in the residue abs. (% by weight) | 27.6 |

EXAMPLE 4.

| Extraction medium: | propane/carbon dioxide |
|---|---|
| mixing ratio | 80/20 |
| Process parameters: | |
| extraction pressure (bar) | 40 |
| extraction temperature (°C.) | 50 |
| SM/AM (kg/kg) | 15 |
| Extract: | |
| yield (% by wt.) | 44.3 |
| phospholipid content (% by wt.) | 1 |
| cholesterol content (% by wt.) | 5.6 |
| Residue (product): | |
| yield (% by wt.) | 57.7 |
| cholesterol content (% by wt.) | 0.18 |
| total fat (% by wt.) | 38.0 |
| phospholipids in the total fat (% by wt.) | 77 |
| phospholipids in the residue abs. (% by wt.) | 29.3 |

EXAMPLE 5.

| Extraction medium: | Propane/carbon dioxide |
|---|---|
| mixing ratio | 70/30 |
| Process parameters: | |
| extraction pressure (bar) | 50 |
| extraction temperature (°C.) | 45 |
| SM/AM (kg/kg) | 30 |
| Extract: | |
| yield (% by wt.) | 38.55 |
| phospholipid content (% by wt.) | 0.2 |
| cholesterol content (% by wt.) | 5.9 |

-continued

| Residue (product): | |
|---|---|
| yield (% by wt.) | 58.4 |
| cholesterol content (% by wt.) | 0.16 |
| total fat (% by wt.) | 39.9 |
| phospholipids in the total fat (% by wt.) | 75 |
| phospholipids in the residue abs. (% by wt.) | 29.9 |

EXAMPLE 6.

| Extraction medium: | propane/carbon dioxide |
|---|---|
| mixing ratio | 30/70 |
| Process parameters: | |
| extraction pressure (bar) | 250 |
| extraction temperature (°C.) | 45 |
| SM/AM (kg/kg) | 75 |
| Extract: | |
| yield (% by wt.) | 38.5 |
| phospholipid content (% by wt.) | 0.15 |
| cholesterol content (% by wt.) | 5.8 |
| Residue (product): | |
| yield (% by wt.) | 58.2 |
| cholesterol content (% by wt.) | 0.18 |
| total fat (% by wt.) | 39.5 |
| phospholipids in the total fat (% by wt.) | 74 |
| phospholipids in the residue abs. (% by wt.) | 29.6 |

EXAMPLE 7.

The starting material (whole egg powder) investigated in this Example had the following composition in the lipid part:

| total fat (% by wt.) | 41.2 |
|---|---|
| cholesterol (% by wt.) | 1.4 |
| phospholipids (% by wt.) | 13.9 |
| Extraction medium: | propane/carbon dioxide |
| mixing ratio | 70/30 |

-continued

| Process parameters: | |
|---|---|
| extraction pressure (bar) | 50 |
| extraction temperature (°C.) | 45 |
| SM/AM (kg/kg) | 25 |
| Extract: | |
| yield (% by wt.) | 25.8 |
| phospholipid content (% by wt.) | 0.2 |
| cholesterol content (% by wt.) | 1.9 |
| Residue (product): | |
| yield (% by wt.) | 73.8 |
| cholesterol content (% by wt.) | 0.12 |
| total fat (% by wt.) | 21.4 |
| phospholipids in the total fat (% by wt.) | 85 |
| phospholipids in the residue abs. (% by wt.) | 18.2 |

We claim:

1. A process for producing an egg-based product in powder form having a reduced fat and cholesterol derivative content, comprising extracting fat and cholesterol derivatives from a powdered egg based product with a solvent mixture comprising propane and carbon dioxide in a ratio of from 95:5% to 5:95% by weight at a pressure of <300 bar and a temperature of <70° C.

2. Process according to claim 1, wherein the ratio of propane to carbon dioxide is from 90:10% to 50:50% by weight.

3. Process according to claim 1, wherein the ratio of propane to carbon dioxide is from 80:20% to 60:40% by weight.

4. Process according to claim 1, wherein the extraction temperature is from 20° to 60° C.

5. Process according to claim 4, wherein the extraction temperature is from 30° to 50° C.

6. Process according to claim 1, wherein the extraction is carried out at a pressure of 10 to 100 bar.

7. Process according to claim 1, wherein 1 to 100 kg of the solvent mixture is used per kg of said powdered egg based product.

8. Process according to claim 1, further comprising separating fat and cholesterol derivatives from the solvent mixture by evaporation or lowering the pressure.

* * * * *